United States Patent
Keller

(10) Patent No.: US 8,517,226 B2
(45) Date of Patent: Aug. 27, 2013

(54) SYRINGE WITH A PISTON

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 1007 days.

(21) Appl. No.: 12/375,143

(22) PCT Filed: Aug. 6, 2007

(86) PCT No.: PCT/CH2007/000382
§ 371 (c)(1),
(2), (4) Date: Jan. 26, 2009

(87) PCT Pub. No.: WO2008/017181
PCT Pub. Date: Feb. 14, 2008

(65) Prior Publication Data
US 2009/0255960 A1    Oct. 15, 2009

(30) Foreign Application Priority Data
Aug. 9, 2006 (CH) ........................... 1285/06

(51) Int. Cl.
*B67D 7/60* (2010.01)
*G01F 11/00* (2006.01)
*A61M 37/00* (2006.01)

(52) U.S. Cl.
USPC ........................................... 222/386; 604/82

(58) Field of Classification Search
USPC ..... 604/82–92, 191, 187, 232, 218; 606/213, 606/214; 222/386
See application file for complete search history.

(56) References Cited

U.S. PATENT DOCUMENTS

| | | | |
|---|---|---|---|
| 2,841,145 A | 7/1958 | Epps | |
| 4,581,016 A | 4/1986 | Gettig | |
| 5,193,907 A * | 3/1993 | Faccioli et al. | 222/137 |
| 5,779,668 A * | 7/1998 | Grabenkort | 604/89 |
| 5,779,683 A * | 7/1998 | Meyer | 604/198 |
| 6,440,101 B1* | 8/2002 | Grabenkort et al. | 604/89 |
| 6,902,543 B1 | 6/2005 | Cherif-Cheikh et al. | |
| 2009/0024082 A1* | 1/2009 | McLean et al. | 604/85 |

FOREIGN PATENT DOCUMENTS

| | | |
|---|---|---|
| FR | 2 656 521 A1 | 7/1991 |
| FR | 2 799 654 A1 | 4/2001 |
| GB | 2 002 241 | 2/1979 |
| JP | 6261932 A | 9/1994 |
| JP | 7246238 A | 9/1995 |
| WO | WO 2006/071758 A1 | 7/2006 |

OTHER PUBLICATIONS

Office Action and English translation issued in corresponding Japanese application No. 2009-523126, issued Jan. 17, 2012; 6 pages.
International Search Report for International Patent Application No. PCT/CH2007/000382, dated Sep. 27, 2007. (3 pgs.).

* cited by examiner

*Primary Examiner* — Matthew F DeSanto
(74) *Attorney, Agent, or Firm* — Foley & Lardner LLP

(57) ABSTRACT

The dispensing assembly with a syringe comprising storage container configured to receive a powdery or granular material and a piston that is connected to a hollow ram. In order to supply a liquid to the powdery or granular material, both the hollow ram and the piston have through-going, sealable longitudinal bores. Due to the fact that the liquid is filled in from the inlet side, a complete de-aeration of the mixture can be ensured.

8 Claims, 5 Drawing Sheets

SYRINGE WITH A PISTON

CROSS-REFERENCE TO RELATED APPLICATIONS

This application is a national stage of International Application no. PCT/CH2007/000382, filed Aug. 6, 2007; which claims the benefit of Switzerland application no. 2006 1285/06, filed Aug. 9, 2006, and priority is hereby claimed under 35 USC §119 based on these applications. Each of these applications are hereby incorporated by reference in their entirety into the present application.

The present invention refers to a dispensing assembly with a syringe or cartridge having a storage container for receiving powdery or granular materials and a piston, the materials being stored and sealed in the syringe or cartridge. Prior to the application of such a material, for example a bone replacement material, a liquid such as a blood or saline solution has first to be added in order to dispense the mixture by means of the piston.

During the admixture of a liquid, if the liquid is sucked in or injected from the front side, i.e. the outlet side, the air enclosed in the storage container is trapped, thereby strongly affecting the application.

Based on this prior art, it is the object of the present invention to prevent that air is entrapped while a liquid is being introduced.

This object is attained by the device according to claim 1.

The invention will be explained in more detail hereinafter with reference to drawings of an exemplary embodiment.

Figure 1:
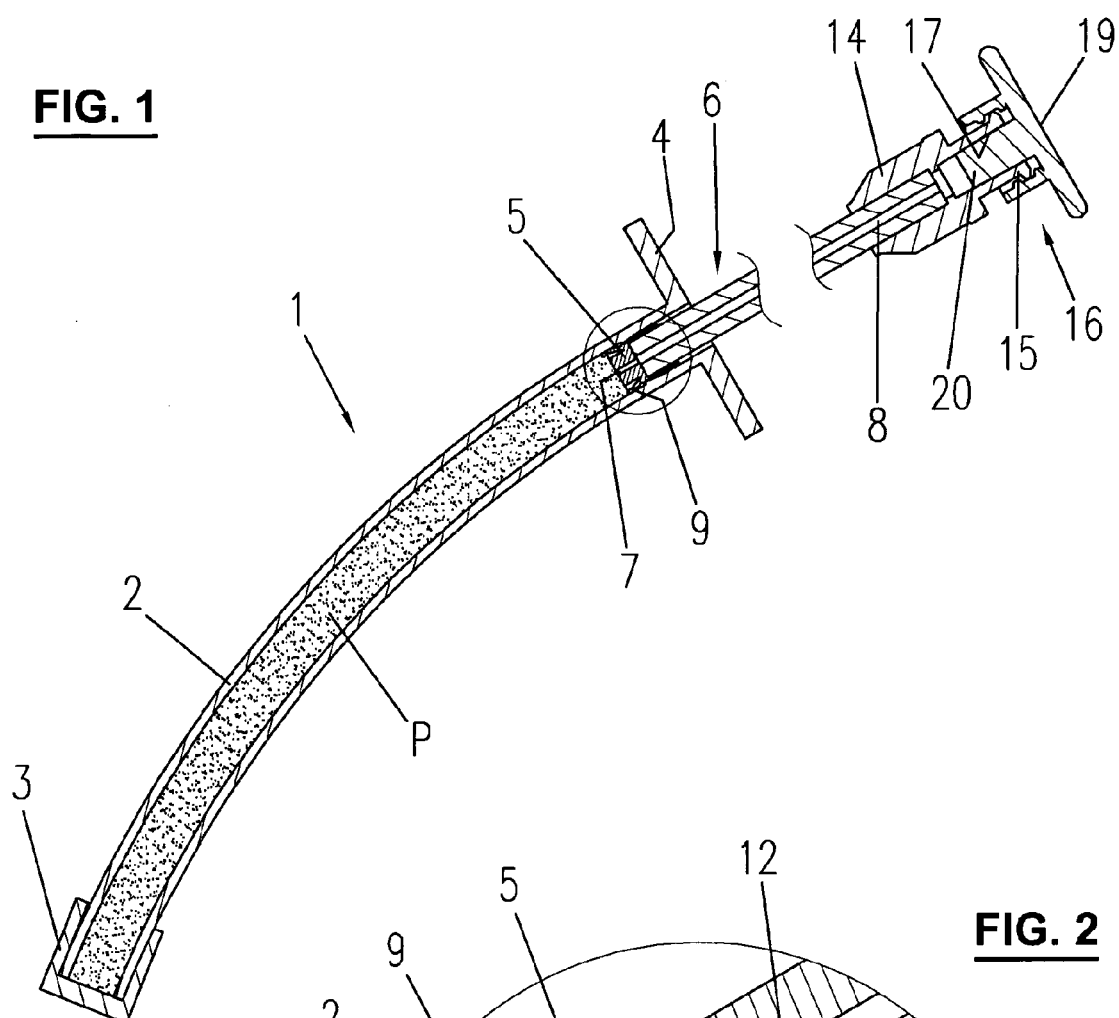
Figure 2:
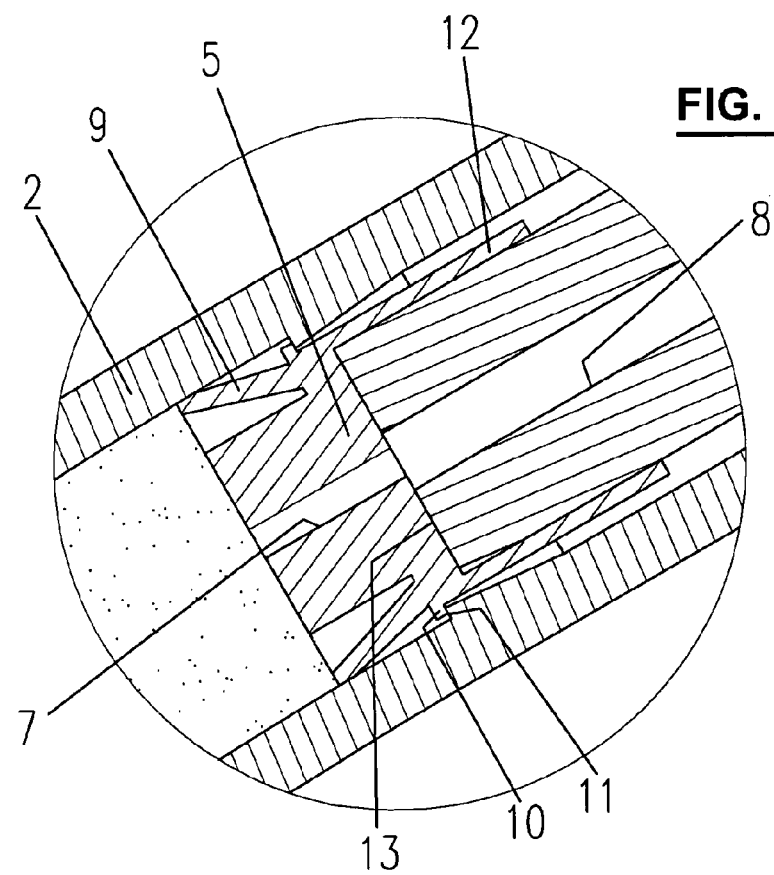
Figure 3:
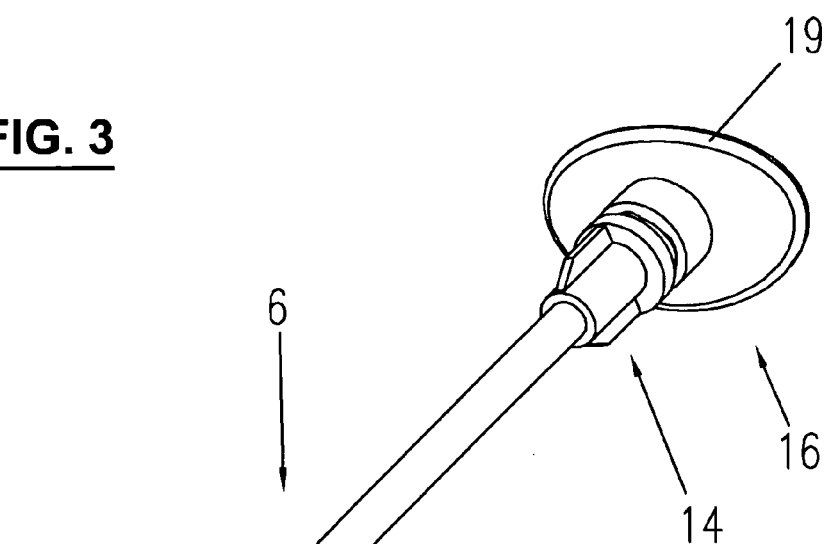
Figure 4:
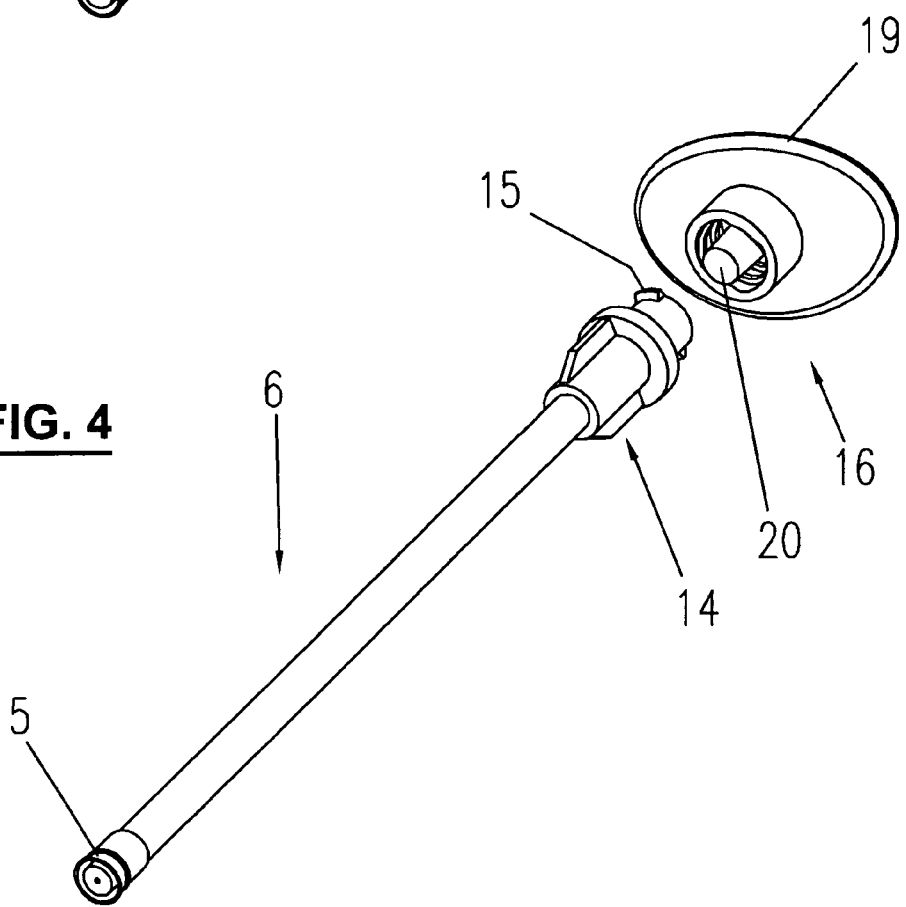
Figure 5:
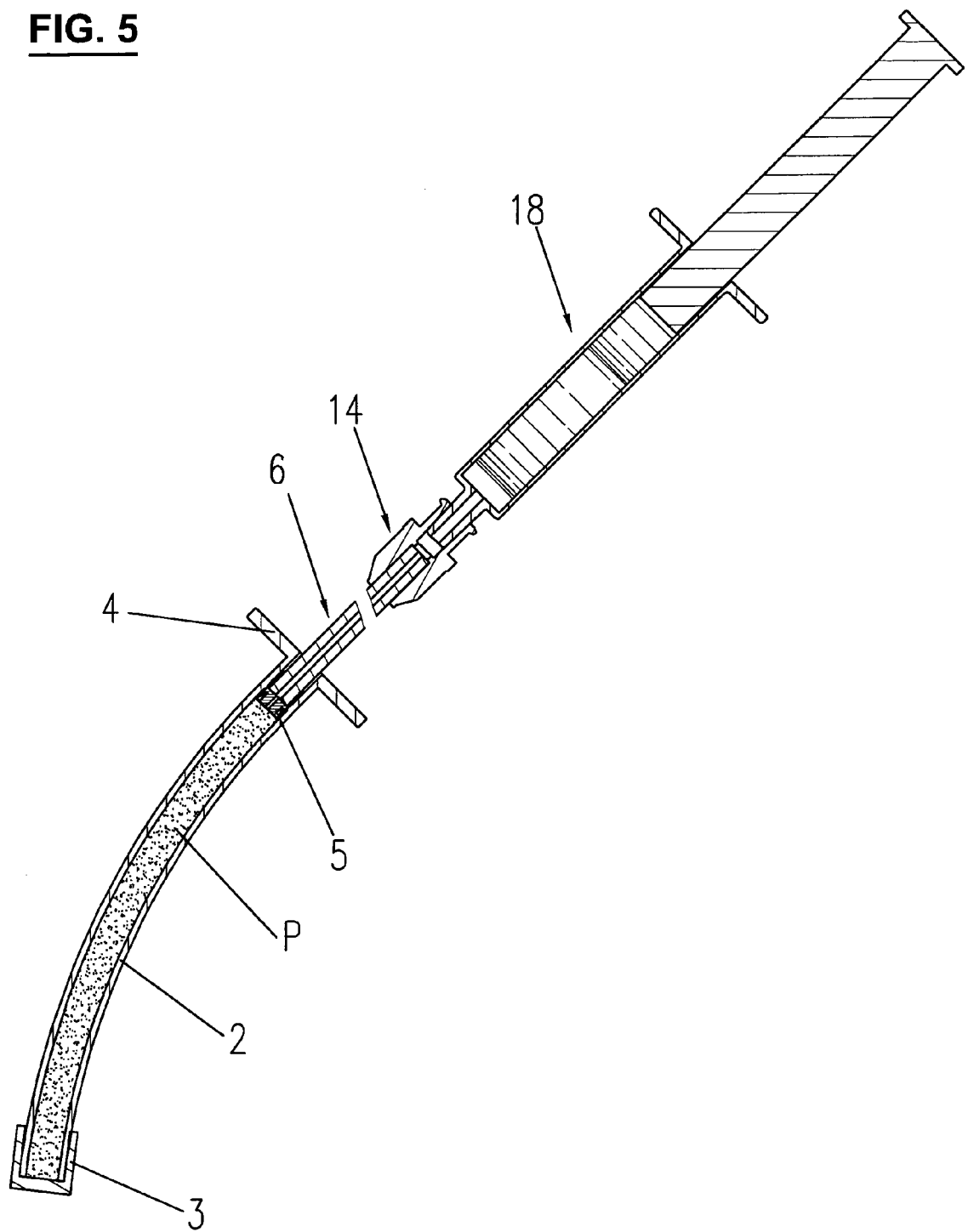
Figure 6:
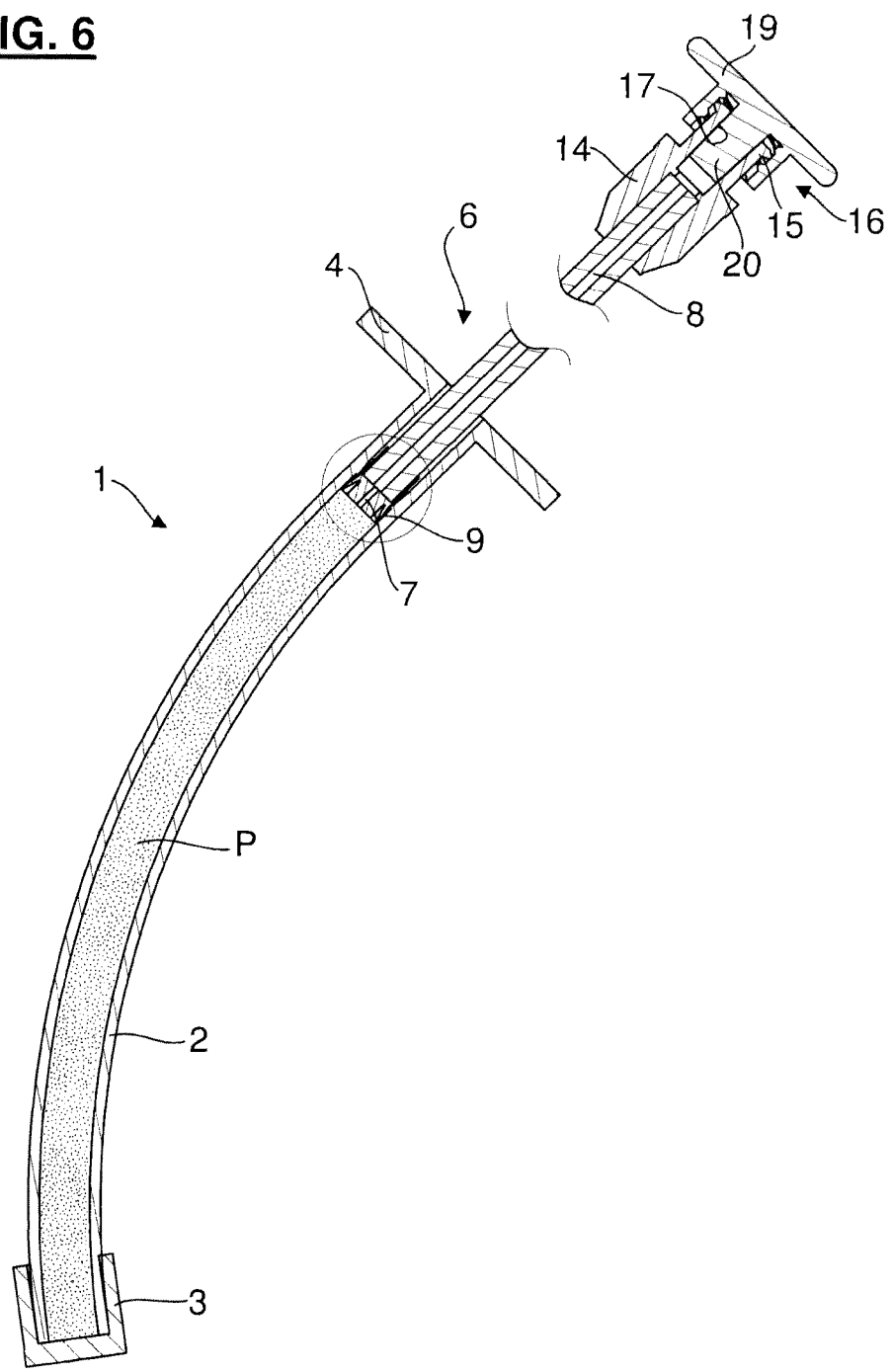
Figure 7:
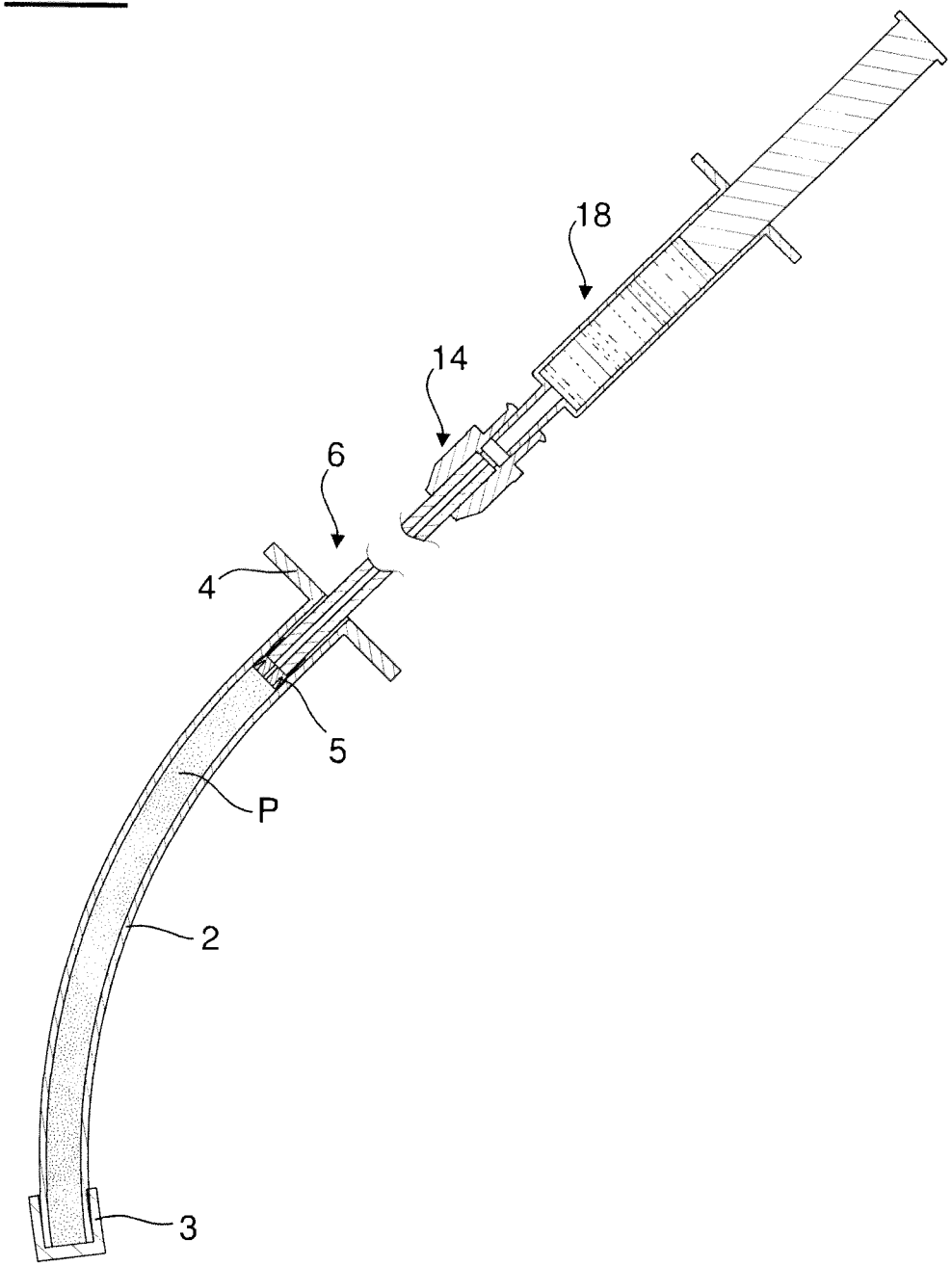

FIG. 1 shows an exemplary embodiment of the invention in a longitudinal section, FIG. 2 shows an enlarged detail of FIG. 1, FIG. 3 shows a part of the device according to the invention in a perspective view and in the assembled condition, FIG. 4 shows the same part as in FIG. 3 in the disassembled condition, FIG. 5 shows the same part as in FIG. 3 in the disassembled condition, and shows a longitudinal section of an exemplary application of the device according to the invention, FIG. 6 shows an exemplary embodiment of a significantly curved storage container in a longitudinal section, and FIG. 7 shows a longitudinal section of FIG. 6 in which a closure has been removed and a separate syringe has been attached.

According to FIG. 1, the dispensing assembly of the invention with a syringe 1 comprises a storage container 2 that is provided at its outlet with a closure cap 3 and on its inlet side with a retaining flange 4 and is filled with a powdery or granular material P. In the present exemplary embodiment, the container is bent and may be made of a flexible material (see FIGS. 6 and 7). On the inlet side, a piston 5 is arranged in container 2 which is connected to a hollow ram 6. Instead of a syringe, the assembly may comprise a cartridge. The term "syringe" stands for both.

As seen in the Figures, both piston 5 and the ram in the form of hollow ram 6 are provided with through-going, generally central bores 7 and 8, respectively.

As appears in FIG. 2, piston 5 has a sealing lip 9 on its outlet side and behind the sealing lip a circumferential collar 10 that prevents, together with a step 11 inside the storage container, that the piston may be pushed out backwards, i.e. toward the inlet side.

Furthermore, at its end 13 facing ram 6, piston 5 has a socket 12 allowing to secure the end of the ram therein, an additional retaining means such as an O-ring possibly being provided which snaps into a circumferential groove inside the socket.

At the end of the hollow ram opposite the piston, a coupling portion 14 is arranged that allows connecting either a closure or a separate syringe. Coupling portion 14 comprises e.g. a Luer-Lock connector 15 to which a closure 16 having a plug 20 is attached. Besides the Luer-Lock connector, other connecting means that are known in the art, such as snap closures or bayonet connecting means, are applicable.

As appears particularly in FIGS. 3 and 4, hollow ram 6 with piston 5 and coupling portion 14 with closure 16 may be embodied as a single unit that is pushed on from the outlet side prior to filling a powdery or granular material into storage container 2. In FIG. 4, the closure is shown in the disassembled condition.

In the illustration of FIG. 5, closure 16 has been removed and a separate syringe 18 has been attached to liquid inlet 17 of coupling portion 14 in order to introduce e.g. a blood or saline solution which subsequently reaches the material P contained in storage container 2 through bores 8 and 7.

After having dispensed the liquid, the separate syringe 18 is removed and closure 16 is replaced. For a better dispensing of the mixture, besides retaining flange 4 on the storage container, the dispensing assembly includes a finger rest 19 on the closure.

As the liquid is supplied by means of a separate syringe, the type and the amount of the liquid can be chosen as desired. While filling in the liquid, air that is enclosed in the storage container is automatically pressed out via the hollow ram since the attachment of the separate syringe inside Luer-Lock liquid inlet 17 is designed so as not to be completely airtight.

The invention claimed is:

1. A dispensing assembly comprising:
   a storage container made of a flexible plastics material, the storage container having a portion configured to receive a powdery or granular material, the portion being significantly curved;
   a piston in the storage container;
   a hollow ram, wherein the piston is connected to the hollow ram, wherein each of the hollow ram and the piston include a through-going longitudinal bore to supply a liquid to the powdery or granular material, wherein an end of the hollow ram, that is opposite to where the piston connects to the hollow ram, comprises a coupling portion, the coupling portion defining a liquid inlet for introducing a liquid through the through-going longitudinal bore of the hollow ram and the through-going longitudinal bore of the piston and into the powdery or granular material in the storage container, the hollow ram and the piston form a seal and follow a contour of the portion of the storage container;
   a removable closure configured to be received in the coupling portion to close the liquid inlet; and
   a separate syringe configured to introduce a liquid through the through-going longitudinal bore of the hollow ram and the through-going longitudinal bore of the piston and into the powdery or granular material in the storage container, the separate syringe configured to connect to the coupling portion after the removable closure is removed from the coupling portion,
   wherein the coupling portion is configured to receive the removable closure or the separate syringe.

2. The dispensing assembly of claim 1, wherein the piston and an interior of the storage container are configured to retain the piston such that the piston is prevented from pushing backwards out of the storage container.

3. The dispensing assembly of claim 2, wherein the piston has a circumferential collar and wherein an inside wall of the storage container has a step, the circumferential collar and the step cooperating such that the piston is prevented from being pushed backwards out of the storage container.

4. The dispensing assembly of claim 1, wherein the piston has a sealing lip and a socket, and wherein the sealing lip and the socket are configured to fasten to the hollow ram.

5. The dispensing assembly of claim 1, wherein the removable closure comprises a finger rest configured to dispense a mixture from the storage container, and wherein the storage container comprises a retaining flange.

6. The dispensing assembly of claim 1, wherein the hollow ram, the piston, the coupling portion, and the removable closure are embodied as a unit that is configured to insert into the storage container.

7. The dispensing assembly of claim 1, wherein the coupling portion comprises one of a Luer-lock connector, a snap closure and a bayonet connector.

8. A method of operating a dispensing assembly comprising:
- a storage container made of a flexible plastics material, the storage container having a portion configured to receive a powdery or granular material, the portion being significantly curved;
- a piston in the storage container;
- a hollow ram, wherein the piston is connected to the hollow ram, wherein each of the hollow ram and the piston include a through-going longitudinal bore to supply a liquid to the powdery or granular material, wherein an end of the hollow ram, that is opposite to where the piston connects to the hollow ram, comprises a coupling portion, the coupling portion defining a liquid inlet for introducing a liquid through the through-going longitudinal bore of the hollow ram and the through-going longitudinal bore of the piston and into the powdery or granular material in the storage container, the hollow ram and the piston form a seal and follow a contour of the portion of the storage container;
- a removable closure configured to be received in the coupling portion to close the liquid inlet; and
- a separate syringe configured to introduce a liquid through the through-going longitudinal bore of the hollow ram and the through-going longitudinal bore of the piston and into the powdery or granular material in the storage container, the separate syringe configured to connect to the coupling portion after the removable closure is removed from the coupling portion,
- wherein the coupling portion is configured to receive the removable closure or the separate syringe, the method comprising:
- removing the removable closure from the coupling portion;
- attaching the separate syringe to the coupling portion;
- dispensing a liquid in the separate syringe through the hollow ram and piston into the powdery or granular material in the storage container;
- removing the separate syringe from the coupling portion after dispensing the liquid;
- replacing the removable closure on the coupling portion; and
- dispensing a mixture from the storage container.

* * * * *

UNITED STATES PATENT AND TRADEMARK OFFICE
CERTIFICATE OF CORRECTION

PATENT NO. : 8,517,226 B2  Page 1 of 1
APPLICATION NO. : 12/375143
DATED : August 27, 2013
INVENTOR(S) : Wilhelm A. Keller It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1089 days.

Signed and Sealed this

Fifteenth Day of September, 2015

Michelle K. Lee
*Director of the United States Patent and Trademark Office*